US005213062A

United States Patent [19]

Canady, Jr.

[11] Patent Number: 5,213,062

[45] Date of Patent: May 25, 1993

[54] PET TRAUMA BOARD

[76] Inventor: James W. Canady, Jr., 117 Hickory Hills Dr., Williamsburg, Va. 23185-5407

[21] Appl. No.: 909,192

[22] Filed: Jul. 6, 1992

[51] Int. Cl.[5] .......................... A61D 3/00; A61G 7/08; A61F 5/37

[52] U.S. Cl. .......................... 119/103; 119/96; 5/89.1; 5/627; 5/628; 128/870; 128/876

[58] Field of Search .......................... 119/103, 96; 5/81.1, 5/89.1, 625-629; 128/870, 871, 876

[56] References Cited

U.S. PATENT DOCUMENTS

| | | | |
|---|---|---|---|
| 1,192,845 | 8/1916 | Bower | 119/103 |
| 1,656,835 | 1/1928 | Simons | 119/103 |
| 3,137,273 | 6/1964 | Greenwood | 119/103 |
| 3,164,131 | 1/1965 | Bradshaw | 119/103 |
| 3,457,585 | 7/1969 | Edison | 119/103 |
| 4,433,643 | 2/1984 | Fraser | 119/103 |
| 4,590,887 | 5/1986 | Holopainen | 119/103 |
| 5,103,769 | 5/1992 | Macintosh | 119/29 |

*Primary Examiner*—John G. Weiss
*Attorney, Agent, or Firm*—Leon Gilden

[57] ABSTRACT

A pet trauma support board structure includes a first board having a second board hingedly mounted thereto, with the first and second boards each including strap apertures to receive a plurality of strap members directed therebetween, with each of the strap members having leg straps, with each of the leg straps including leg strap fastening structure to permit securement of each leg strap about an individual leg of an associated animal. An necessary, an accessory strap is arranged to include a muzzle restraint loop securable about an animal's head.

4 Claims, 5 Drawing Sheets

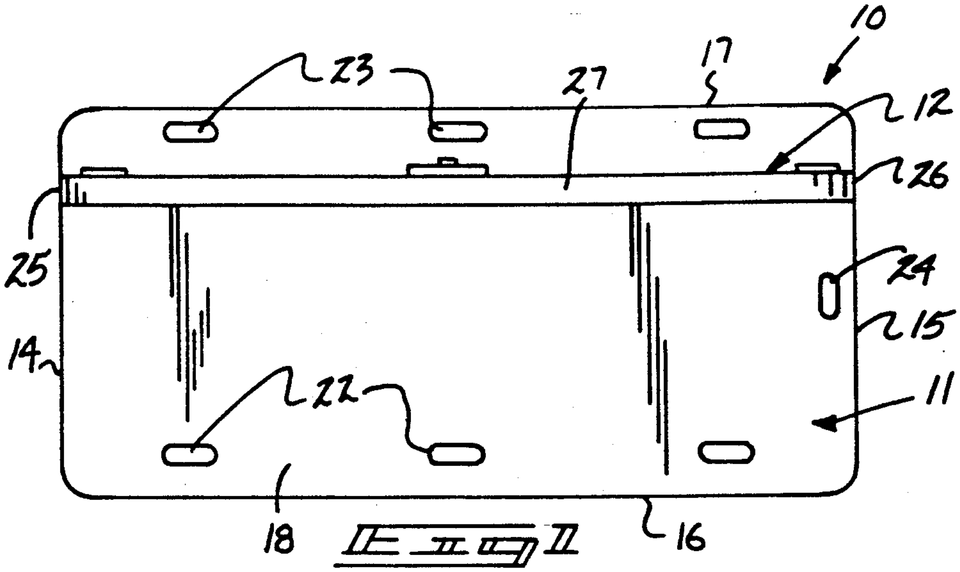
Fig. 1
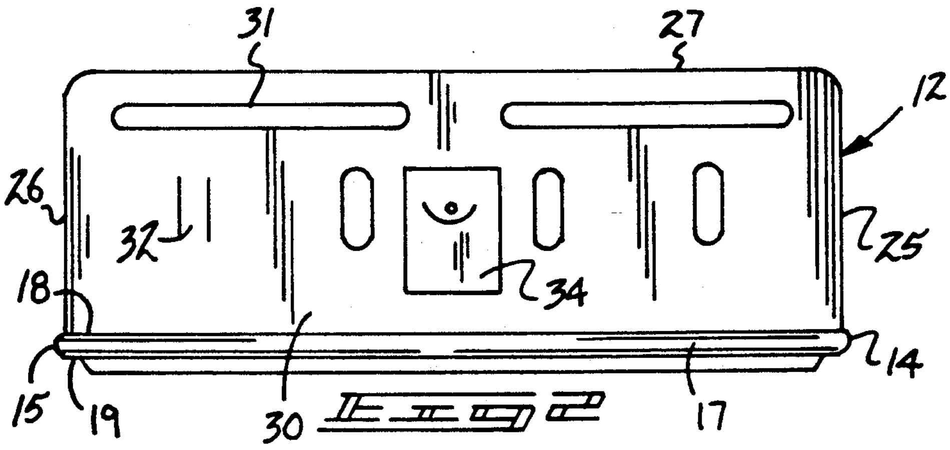
Fig. 2
Fig. 3
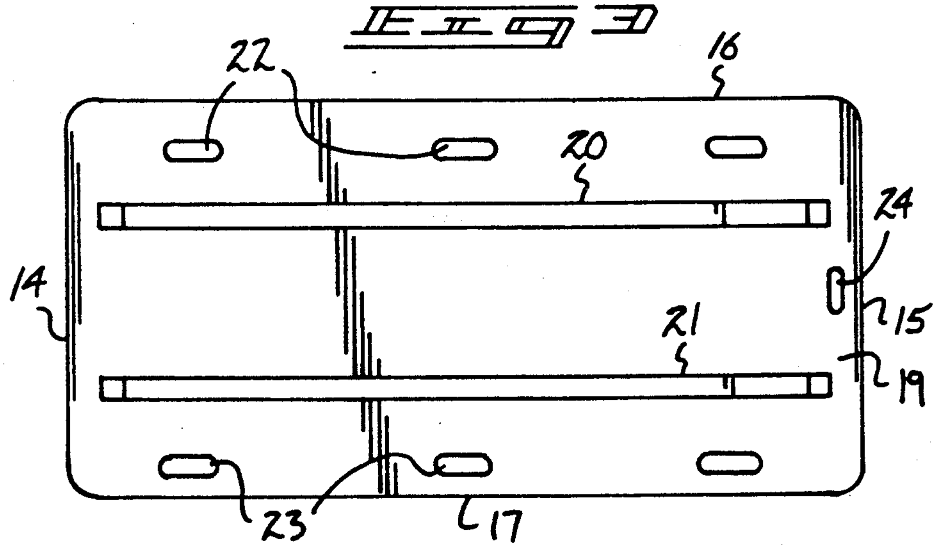

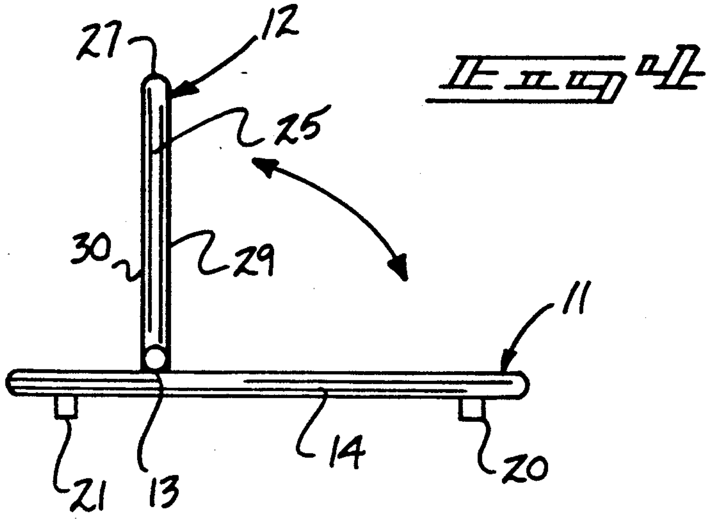
FIG 4
FIG 5
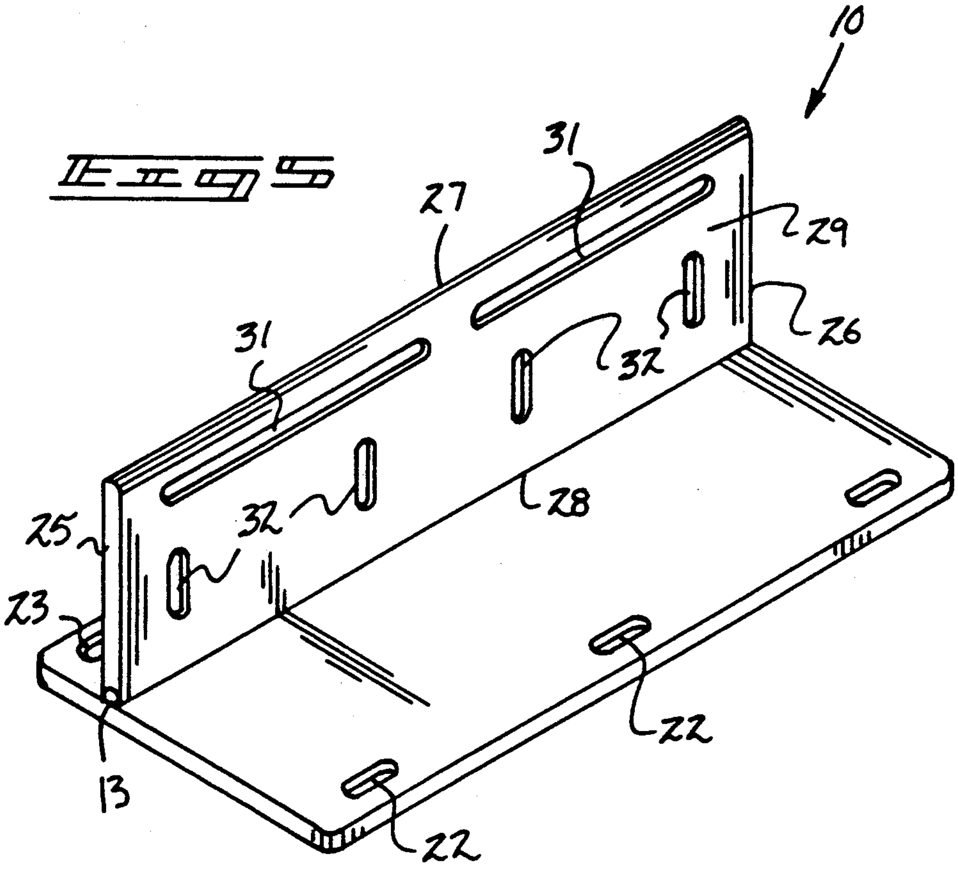

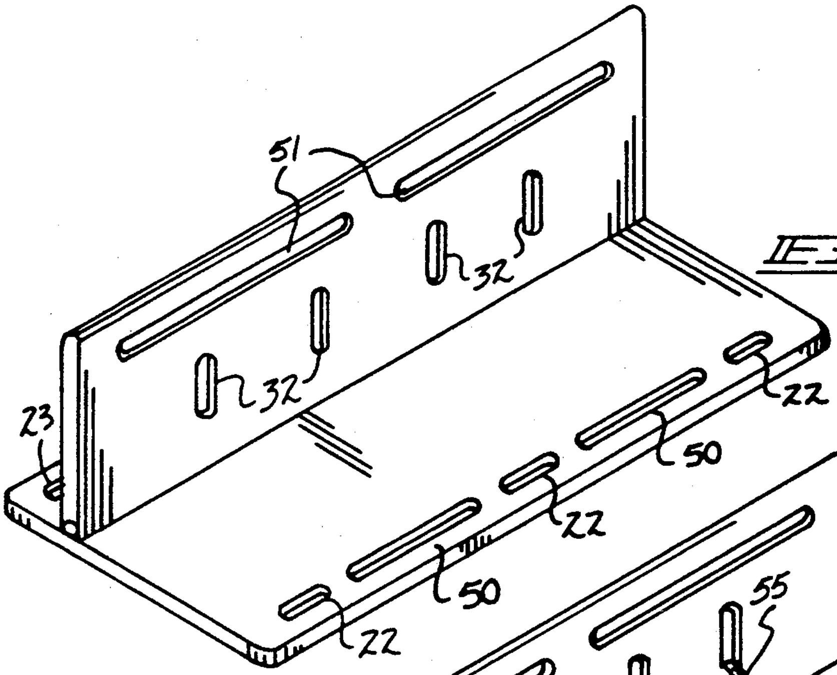
Fig. 10
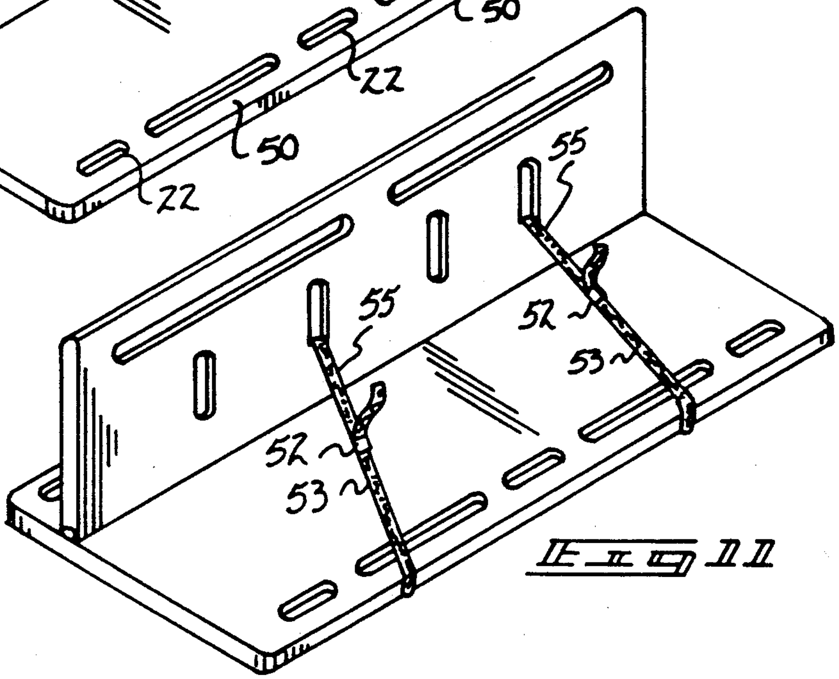
Fig. 11
Fig. 12
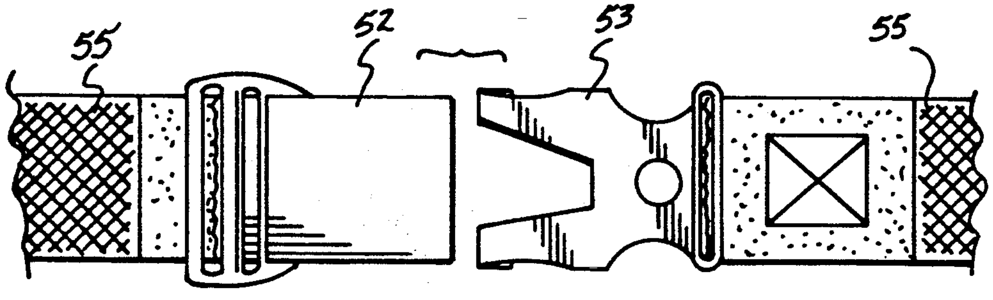

PET TRAUMA BOARD

BACKGROUND OF THE INVENTION

1. Field of the Invention

The field of invention relates to trauma board structure, and more particularly pertains to a new and improved pet trauma board to permit transport of animals.

2. Description of the Prior Art

Injury to pet and farm animals can effect further injury if the animal is not transported properly. While trauma board structure is arranged in the prior art for typical use with the transport of individuals, such structure has heretofore not been particularly configured in a manner as set forth by the instant invention to accommodate transport of pets and the like for further medical treatment. Prior art trauma board structure is exemplified in the U.S. Pat. Nos. 4,612,678; 4,947,418; 3,597,773; and 4,873,732.

Accordingly, it may be appreciated that there continues to be a need for a new and improved pet trauma board as set forth by the instant invention which addresses both the problems of ease of use as well as effectiveness in construction and in this respect, the present invention substantially fulfills this need.

SUMMARY OF THE INVENTION

In view of the foregoing disadvantages inherent in the known types of trauma board structure now present in the prior art, the present invention provides a pet trauma board wherein the same is arranged to position and secure an animal for transport for further medical treatment. As such, the general purpose of the present invention, which will be described subsequently in greater detail, is to provide a new and improved pet trauma board which has all the advantages of the prior art trauma board apparatus and none of the disadvantages.

To attain this, the present invention provides a pet trauma support board structure including a first board having a second board hingedly mounted thereto, with the first and second boards each including strap apertures to receive a plurality of strap members directed therebetween, with each of the strap members having leg straps, with each of the leg straps including leg strap fastening structure to permit securement of each leg strap about an individual leg of an associated animal. As necessary, an accessory strap is arranged to includes a muzzle restraint loop securable about an animal's head.

My invention resides not in any one of these features per se, but rather in the particular combination of all of them herein disclosed and claimed and it is distinguished from the prior art in this particular combination of all of its structures for the functions specified.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto. Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new and improved pet trauma board which has all the advantages of the prior art trauma board apparatus and none of the disadvantages.

It is another object of the present invention to provide a new and improved pet trauma board which may be easily and efficiently manufactured and marketed.

It is a further object of the present invention to provide a new and improved pet trauma board which is of a durable and reliable construction.

An even further object of the present invention is to provide a new and improved pet trauma board which is susceptible of a low cost of manufacture with regard to both materials and labor, and which accordingly is then susceptible of low prices of sale to the consuming public, thereby making such pet trauma boards economically available to the buying public.

Still yet another object of the present invention is to provide a new and improved pet trauma board which provides in the apparatuses and methods of the prior art some of the advantages thereof, while simultaneously overcoming some of the disadvantages normally associated therewith.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 1 is an orthographic top view of the instant invention.

FIG. 2 is an orthographic side view of the instant invention.

FIG. 3 is an orthographic bottom view of the instant invention.

FIG. 4 is an orthographic end view of the instant invention.

FIG. 5 is an isometric illustration of the invention.

FIG. 10 is an isometric illustration of the invention utilizing a repositioning of the various slots and the like in a manner to accommodate animals.

FIG. 11 is an isometric illustration of the invention utilizing strap structure for securement of animals thereto.

FIG. 12 is an orthographic view of connector structure utilized by the invention.

DESCRIPTION OF THE PREFERRED EMBODIMENT

Figure 6:
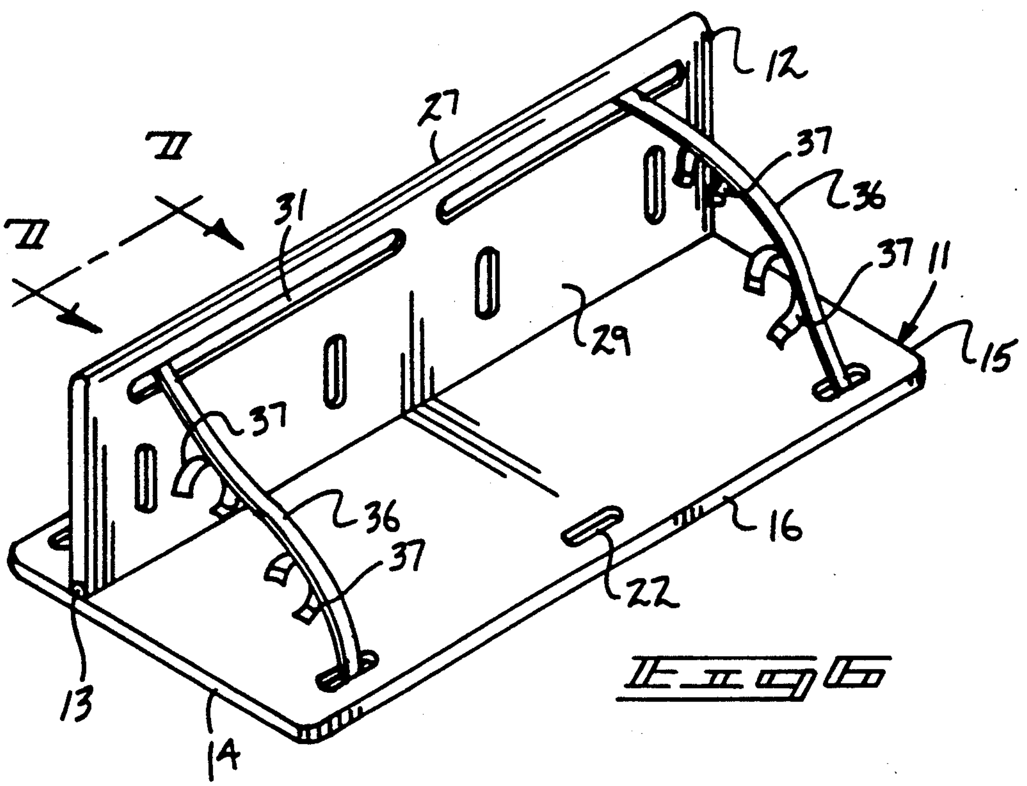
FIG. 6 is an isometric illustration of the invention utilizing body straps.

With reference now to the drawings, and in particular to FIGS. 1 to 12 thereof, a new and improved pet trauma board embodying the principles and concepts of the present invention and generally designated by the reference numeral 10 will be described.

Figure 7:
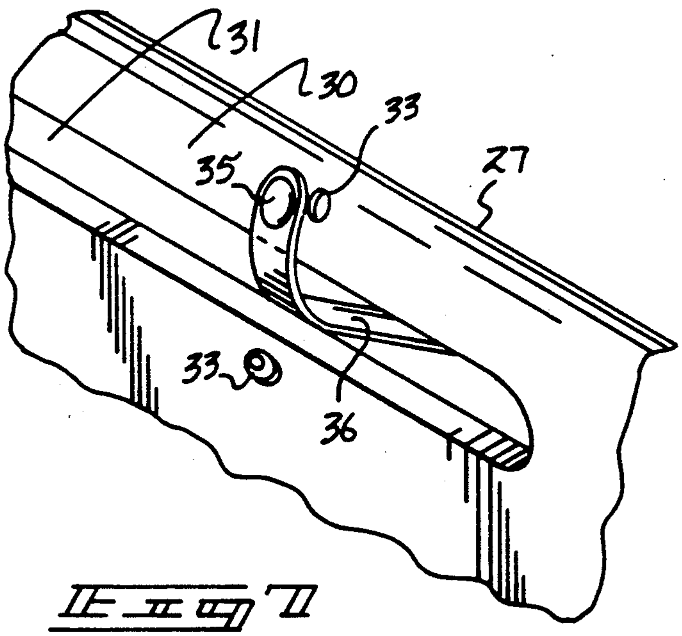
FIG. 7 is an isometric illustration, taken along the lines 7—7 of FIG. 6 in the direction indicated by the arrows.
Figure 8:
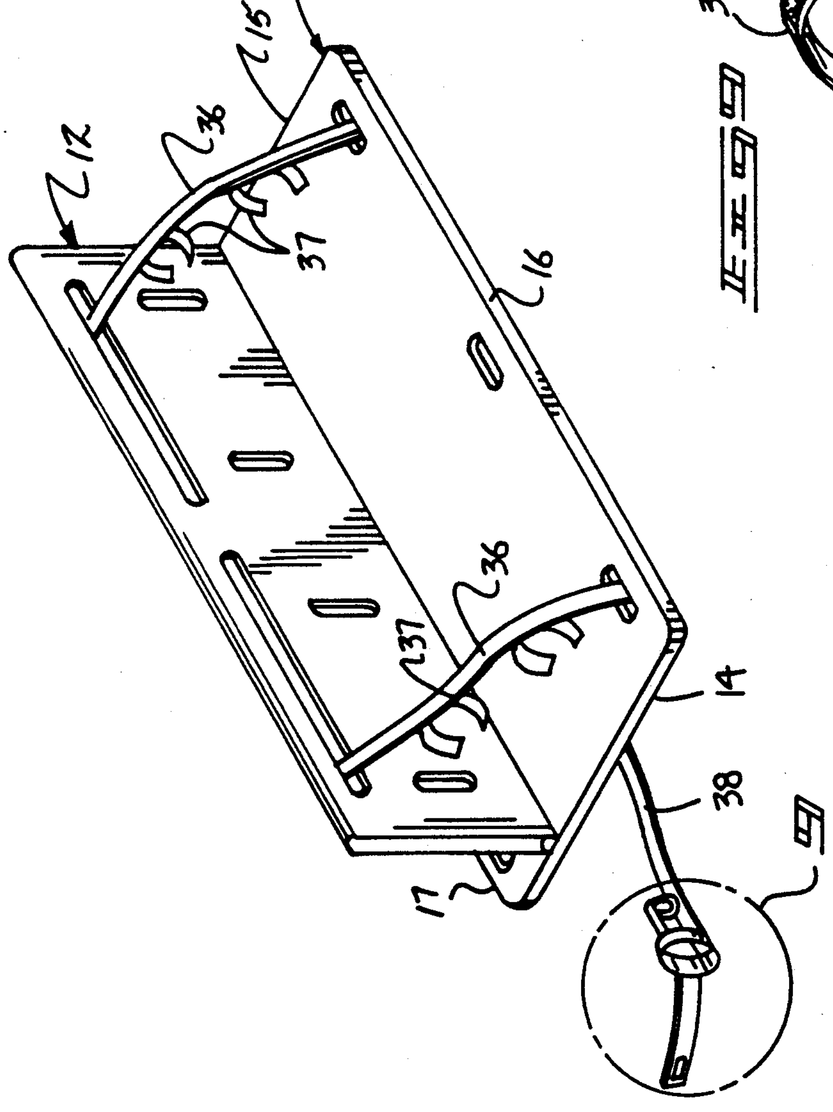
FIG. 8 is an isometric illustration of the invention illustrating the use of a muzzle restraint strap structure.
Figure 9:
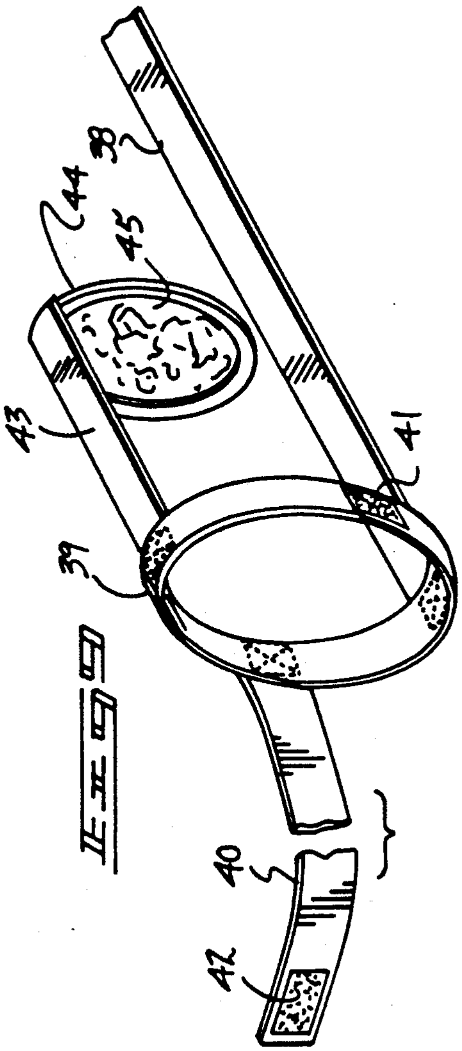
FIG. 9 is an enlarged isometric illustration of section 9 as set forth in FIG. 8.

More specifically, the pet trauma board 10 of the instant invention essentially comprises a first board 11 hingedly mounted to a second board 12 about a hinge member 13 to bias the first board 11 towards the second board 12 for ease of transport of the organization. The first board 11 is formed with a first board first end 14 spaced from and parallel a first board second end 15, a first board first side 16 parallel to and spaced from a first board second side 17, and a first board top surface 18 coextensive with a first board bottom surface 19. The second board 12 is formed with a second board first end 25 spaced from and parallel a second board second end 26, a second board first side 27 parallel to a second board second side 28, and a second board first surface 29 coextensive with and generally parallel to a second board second surface 30. The spring hinge 13 is mounted to the second board second side 28 that is orthogonally directed between the first board first end 14 and the first board second end 15, with the hinge 13 oriented parallel and spaced relative to the second board second side 17, with, as illustrated, second strap apertures 23 oriented between the spring hinge 13 and the first board second side 17, with first board having first strap apertures 22 directed in adjacency in a row along the first board first side 16. The first board bottom surface 19 includes a respective first and second skid flange 20 and 21 oriented parallel to one another and orthogonally between the first board first and second ends 14 and 15 mounted to the first board bottom surface 19. The second board is further formed with second board first side slots 31 oriented parallel to and adjacent the second board first side 27 in adjacency thereto and are longitudinally aligned relative to one another to receive body straps, to be described in more detail below. Second board body slots 32 are directed through the second board in a parallel relationship relative to the first and second ends 25 and 26 and orthogonally oriented relative to the first side slots 31. First snap fastener connectors 33 are mounted to the second board second surface 30 between the second board side slots 31 and the second board first side 27, as illustrated in FIG. 7, to receive the first end of respective body straps 36 that are directed through the slots 31 having second snap fastener connectors 35 mounted to the first ends of the body straps, with the second ends of the body straps arranged for projection through the first strap apertures 22 and fixedly mounted to the first board 11 in any convenient manner to utilize adhesives, fasteners, and the like. Each of the body straps 36 includes a plurality of leg straps 37 that are oriented between the first board first side 16 and the first side slots 31. Each of the leg straps 37 includes fastener structure to provide for securement of each of the leg straps relative to one another to secure an animal's leg. Typically, hook and loop fastener structure is utilized, as illustrated.

As required, a muzzle strap 38 is provided having a muzzle strap loop 39 mounted at its distal end spaced from the first board first end 14. The muzzle strap loop 39 includes a loop fastener strap 40 projecting therefrom for securement about an animal's head having a hook and loop fastener patch 41 mounted to the muzzle strap loop 39 and a fastener strap hook and loop fastener patch 42 mounted to the distal end of the fastener strap 40. An accessory strap 43 is mounted to the muzzle strap loop 39 having an accessory strap first end secured to the loop 39 and a second end having a container member 44 secured thereto. The container member 44 includes fibrous wadding 45 containing typically an anesthetic fluid therewithin to effect calming of an animal secured to the organization to prevent additional injury due to squirming and the like of an animal experiencing pain and discomfort.

Further it should be noted that a support aperture 24 is directed through the first board 11 in adjacency and medially of the first board second end 15. In this manner, during periods of non-use and storage of the organization, the second board's first surface 29 is biased towards the first board's top surface 18, wherein the support aperture permits mounting and positioning of the organization upon a support peg or the like for convenience and compactness of configuration.

It should be further noted that the second board body slots 32 are provided to accommodate animals of lesser height to permit directing the body straps 36 through the second board body slots for subsequent securement to the first snap fastener connectors 33.

The FIGS. 10 and 11 of the invention indicate the second board body slots 32 positioned inwardly of the second board 12 to more readily accommodate animals to employ connector belts 55 having first and second connector members 52 and 53 to secure the animals relative to the belt structure.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by Letters Patent of the United States is as follows:

1. A pet trauma board, comprising, a first board, including a first board first end spaced from and parallel a first board second end, a first board first side spaced from and parallel a first board second side, and a first board top surface parallel to and coextensive relative to a first board bottom surface, and a second board, the second board having a second board first end spaced from and parallel a second board second end, the second board first side spaced from and parallel a second board second side, a second board first surface parallel to and coextensive relative to a second board second surface, and a spring hinge member means mounted to the second board second side and to the first board top surface for biasing the second board first surface towards the first board top surface, and the first board first end is spaced from the first board second end a predetermined length, and the second board first end is spaced from the second board second end said predetermined length, with the second board orthogonally oriented and coextensive relative to the first board first end and the first board second end, and including a plurality of first strap apertures directed through the first board in a longitudinally aligned relationship parallel to the first board first side, and a plurality of second apertures arranged in a longitudinally aligned row parallel to the first board second side oriented between the second board second side and the first board second side, and the second board including second board first side slots arranged longitudinally aligned relative to one another and parallel to and in adjacency to the second board first side, and a plurality of second board body slots orthogonally oriented relative to the second board first side slots directed through the second board.

2. A pet trauma board as set forth in claim 1 wherein a plurality of body straps are provided, the body straps having a first end, the body strap first end including a second snap fastener, and the second board including a plurality of first snap fasteners, wherein the first snap fasteners are mounted to the second board second surface between the second board first side slots and the second board first side, and the body straps extend between the second board first side slots and the first strap apertures of the first board, and each of the body straps include a plurality of leg straps, with the leg straps oriented between the first board and the second board, and each of the body straps including fastening means for securement of the body straps relative to one another for securement about an animal's leg member.

3. A pet trauma board as set forth in claim 2 including a muzzle strap, the muzzle strap having a muzzle strap first end and a muzzle strap second end, the muzzle strap first end secured to the first board in adjacency to the first board first end, the muzzle strap second end including a muzzle strap loop, the muzzle strap loop including a fastener strap secured thereto in a spaced relationship relative to the muzzle strap, the fastener strap having a first end secured to the muzzle strap loop, and a fastener strap second end, with the muzzle strap second end including a second hook and loop fastener patch and the loop including a loop hook and loop fastener patch secured to the second end hook and loop fastener patch.

4. A pet trauma board as set forth in claim 3 wherein the muzzle strap loop includes an accessory strap, the accessory strap having an accessory strap first end secured to the muzzle strap loop between the fastener strap and the muzzle strap, with the accessory strap having an accessory strap second end, the accessory strap second end including a container member secured thereto, the container member including a fibrous wadding, with the fibrous wadding receiving an anesthetic fluid therewithin.

* * * * *